United States Patent
Jeong et al.

(10) Patent No.: US 12,350,459 B2
(45) Date of Patent: Jul. 8, 2025

(54) MICROSTRUCTURE-BASED DRUG INJECTION DEVICE AND METHOD FOR MANUFACTURING THE SAME

(71) Applicants: KOREA INSTITUTE OF MACHINERY & MATERIALS, Daejeon (KR); ADM BIOSCIENCE INC., Daejeon (KR)

(72) Inventors: Jun Ho Jeong, Daejeon (KR); So Hee Jeon, Daejeon (KR); Ki Don Kim, Daejeon (KR); Seok Min Yoon, Daejeon (KR); Joo Buom Lee, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 1087 days.

(21) Appl. No.: 17/277,638

(22) PCT Filed: Sep. 18, 2019

(86) PCT No.: PCT/KR2019/012085
§ 371 (c)(1),
(2) Date: Mar. 18, 2021

(87) PCT Pub. No.: WO2020/060195
PCT Pub. Date: Mar. 26, 2020

(65) Prior Publication Data
US 2022/0023604 A1 Jan. 27, 2022

(30) Foreign Application Priority Data
Sep. 18, 2018 (KR) .................. 10-2018-0111529

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0024* (2013.01); *A61K 9/0097* (2013.01);
(Continued)

(58) Field of Classification Search
CPC .................................................. A61K 9/0024
See application file for complete search history.

(56) References Cited

U.S. PATENT DOCUMENTS

| | | |
|---|---|---|
| 2002/0138049 A1 | 9/2002 | Allen et al. |
| 2018/0015272 A1* | 1/2018 | Kim ............. A61L 31/146 |
| 2018/0133448 A1 | 5/2018 | Jung et al. |

FOREIGN PATENT DOCUMENTS

| | | |
|---|---|---|
| EP | 2 283 809 A1 | 2/2011 |
| EP | 3 017 841 A1 | 5/2016 |

(Continued)

OTHER PUBLICATIONS

Woo Lee et al (Journal of Drug Targeting, 2013; 21(3): 211-223). (Year: 2013).*

(Continued)

*Primary Examiner* — Benjamin J Packard
(74) *Attorney, Agent, or Firm* — Hauptman Ham, LLP

(57) ABSTRACT

A method for manufacturing a microstructure-based drug injection device according to an embodiment of the present invention includes: a forming mold preparation step for preparing a forming mold formed in a shape corresponding to a microstructure to be manufactured; a biodegradable material-mixed solution application step for applying a biodegradable material-mixed solution to the forming mold; a primary drying step for drying the biodegradable material-mixed solution applied to the forming mold and forming a needle film in which the microstructure is formed; a drug filling step for filling a drug into a filling space formed by the microstructure; and a secondary drying step for drying the (Continued)

needle film, wherein, in the filling space that has undergone the secondary drying step, an inner space portion is formed in a region other than in the region in which the drug is accommodated.

15 Claims, 14 Drawing Sheets

(51) Int. Cl.
  *A61K 9/16*   (2006.01)
  *B29C 39/02*  (2006.01)
  *B29C 39/22*  (2006.01)
  *B29L 31/00*  (2006.01)

(52) U.S. Cl.
  CPC .............. *A61K 9/16* (2013.01); *B29C 39/026* (2013.01); *B29C 39/22* (2013.01); *A61M 2037/0023* (2013.01); *A61M 2037/0053* (2013.01); *B29K 2995/006* (2013.01); *B29L 2031/7544* (2013.01)

(56) References Cited

FOREIGN PATENT DOCUMENTS

| | | |
|---|---|---|
| EP | 3 266 493 A1 | 1/2018 |
| JP | 2009-233808 A | 10/2009 |
| JP | 2015-116335 A | 6/2015 |
| JP | 2016-158930 A | 9/2016 |
| JP | 2017-38781 A | 2/2017 |
| KR | 10-1746024 B1 | 6/2017 |
| KR | 10-1776659 B1 | 9/2017 |
| KR | 10-1785766 B1 | 10/2017 |

OTHER PUBLICATIONS

International Search Report dated Jan. 16, 2020, in connection with corresponding International Patent Application No. PCT/KR2019/012085.

PCT Written Opinion dated Jan. 16, 2020, in connection with corresponding International Patent Application No. PCT/KR2019/012085.

The extended European Search Report dated May 23, 2022 for corresponding European Patent Application No. 19863606.0.

* cited by examiner

MICROSTRUCTURE-BASED DRUG INJECTION DEVICE AND METHOD FOR MANUFACTURING THE SAME

CROSS-REFERENCE TO RELATED APPLICATION

The present application is a national stage filing under 35 U.S.C § 371 of PCT application number PCT/KR2019/012085 filed on Sep. 18, 2019 which is based upon and claims the benefit of priorities to Korean Patent Application No. 10-2018-0111529, filed on Sep. 18, 2018, in the Korean Intellectual Property Office, which are incorporated herein in their entireties by reference.

TECHNICAL FIELD

The present invention relates to a microstructure-based drug injection device, and a manufacturing method thereof. More particularly, the present invention relates to a microstructure-based drug injection device in which an inner space is formed in an area other than an area in which a drug is accommodated in a filling space, the filled drug penetrates into a hole formed in the microstructure, and the drug is distributed not only in the filling space but also at a front end of the microstructure such that the shape of the microstructure can be maintained, drug leakage can be prevented, and skin penetration and delivery efficiency of effective components contained in drugs can be improved, and a manufacturing method thereof.

BACKGROUND ART

In general, a drug delivery system (DDS) means a series of technologies that control the delivery of pharmacologically active materials to cells, tissues, organs, and the body to exert optimal effects using various physicochemical techniques.

These drug delivery systems include an oral drug delivery system in which drugs are taken orally and a transdermal drug delivery system in which drugs are injected locally using a syringe.

The transdermal drug delivery system has been recognized as important for a long time because it can efficiently and safely administer pharmaceutical materials such as drugs, but it has problems of accompanying pain and temporary injection of drugs.

In order to improve the drawback of such a syringe, a micro-sized transdermal needle, which is much smaller than a syringe, is manufactured and used.

Such micro-sized needles are used as a device for injecting drugs for skin beauty or treatment into skin tissue, or for extracting bodily fluids such as blood from the inside of the skin, and are used in many fields such as the treatment of skin diseases or preventive injections of diseases.

Methods of delivering drugs using these microneedles include coating the drug on the needle surface and filling the drug inside the needle, and when a drug is filled inside the needle, the needle is formed of a biodegradable material and thus the needle penetrates the skin, and the filled drug is injected into the skin tissue by dissolving the needle in the area penetrating the skin.

However, most microneedles inject drugs without voids in the biodegradable material, and the shape of the microneedles shrinks due to the penetration of the drug into the biodegradable material during the manufacturing process, or the filled drug leaks out of the microneedles. In addition, since the drug cannot be injected during the dissolving time of the needle formed of the biodegradable material, it is difficult to inject the drug immediately, and the penetration of the skin and the delivery efficiency may be deteriorated.

DISCLOSURE

Technical Problem

One aspect of the present invention is to provide a microstructure-based drug injection device in which an inner space is formed in an area other than the area in which a drug is accommodated in a filling space, the filled drug penetrates into a hole formed in the microstructure, and the drug is distributed not only in the filling space but also at a front end of the microstructure such that the shape of the microstructure can be maintained, drug leakage can be prevented, and skin penetration and delivery efficiency of effective components contained in drugs can be improved, and a manufacturing method thereof.

Technical Solution

A method for manufacturing a microstructure-based drug injection device according to an embodiment of the present invention includes: preparing a forming mold having a shape that corresponds to a microstructure to be manufactured; applying a biodegradable material-mixed solution to the forming mold; primary drying to form a needle film where the microstructure is formed by drying the biodegradable material-mixed solution applied to the forming mold; drug filling for filling a drug in a filling space formed by the microstructure; and secondary drying for drying the needle film, wherein an inner space is formed in an area other than an area where the drug is accommodated in the filling space that has undergone the secondary drying.

Here, the drug filled in the filling space is in a fluid state in drug filling, and at least a part of the drug filled in the filling space is permeated into the microstructure in the drug filling.

In addition, a droplet diameter of the drug filled in the filling space in the drug filling may have a range within 1000 μm.

In addition, the method for manufacturing the microstructure-based drug injection device may further include, before the drug filling, manufacturing a solid-state drug filled in the filling space, wherein the manufacturing of the solid-state drug may include: fluid-state drug filling for filling a fluid-state drug in a solid drug manufacturing mold; mold combining in which a shaping mold that corresponds to a shape of the solid-state drug to be manufactured is combined with the solid drug manufacturing mold; and drug treatment in which the drug is treated to be phase-changed to the solid-state drug from the liquid-state drug.

In the mold combining, the shaping mold may form the drug in the shape of a triangle that corresponds to an inner shape of the filling space, while disposing the drug in a part of the filling space, and may be combined with the solid drug manufacturing mold.

In the mold combining, the shaping mold may form the drug in the shape of a "V", while disposing one part of the drug in a part of the filling space and disposing the other part outside the filling space, and may be combined with the solid drug manufacturing mold.

In addition, in the mold combining, the shaping mold may form the drug in the shape of a "V", while disposing the drug in a part of the filling space, and may be combined with the solid drug manufacturing mold.

According to another embodiment of the present invention, a method for manufacturing a microstructure-based drug injection device can be provided. The method includes: preparing a forming mold having a shape that corresponds to a microstructure to be manufactured; applying a biodegradable material-mixed solution to the forming mold; primary drying to form a needle film where the microstructure is formed by drying the biodegradable material-mixed solution applied to the forming mold; coating a drug to an outer surface of the microstructure; and secondary drying for drying the needle film, wherein an inner space where a gas is accommodated is formed in a filling space formed by the microstructure in the primary drying.

In addition, a microstructure-based drug injection device according to an embodiment of the present invention includes: a needle film where a microstructure is formed; a drug filled in at least a part of a filling space formed by the microstructure; and an inner space that corresponds to a space other than an area where the drug is accommodated in the filling space, while accommodating a gas.

Here, the drug is in a fluid state, and at least a part of the drug filled in the filling space may be permeated into the microstructure.

In addition, a droplet diameter of the drug may have a range within 1000 μm.

In addition, the drug may be in a solid state, and the drug may be formed in the shape of a triangle that corresponds to an inner shape of the filling space, and may be disposed in at least a part of the filling space.

In addition, the drug may be in a solid state, and the drug may be formed in the shape of a "V", while a part of the drug is disposed in at least a part of the filling space and the other part is disposed outside the filling space.

In addition, the drug may be in a solid state, and the drug may be formed in the shape of a "V", and thus may be disposed in at least a part of the filling space.

In addition, a microstructure-based drug injection device according to another embodiment of the present invention includes: a needle film where a microstructure is formed; a drug coated to an outer surface of the microstructure; and an inner space of which at least a part is disposed in a filling space formed by the microstructure.

Advantageous Effects

The microstructure-based drug injection device and the manufacturing method thereof according to the embodiment of the present invention have the following effects.

First, the drug filled in the filling space penetrates into the hole formed in the microstructure, and the drug is distributed not only in the filling space but also at the front end of the microstructure, thereby improving the skin penetration and delivery efficiency of the effective components contained in the drug.

Second, there is an advantage that an internal space is formed inside the microstructure and thus the shrinkage of the microstructure in the drying step can be reduced such that the microstructure of which the shape is close to that of the forming mold can be manufactured.

Third, when the microstructure is inserted into the subcutaneous tissue and dissolved, the inner space is formed in the microstructure and thus an area where the inner space is disposed rapidly dissolves such that a needle film attached with a patch film can be quickly separated from the skin while the microstructure of the drug-filled area is being inserted into the subcutaneous tissue.

Fourth, when an external force is applied and thus the needle film is attached to the skin and the microstructure is inserted into the subcutaneous tissue, the inner space is formed in the microstructure such that the drug contained in the microstructure can be prevented from being leaked out of the needle film and the patch film due to the external force.

MODE FOR INVENTION

Figure 1:
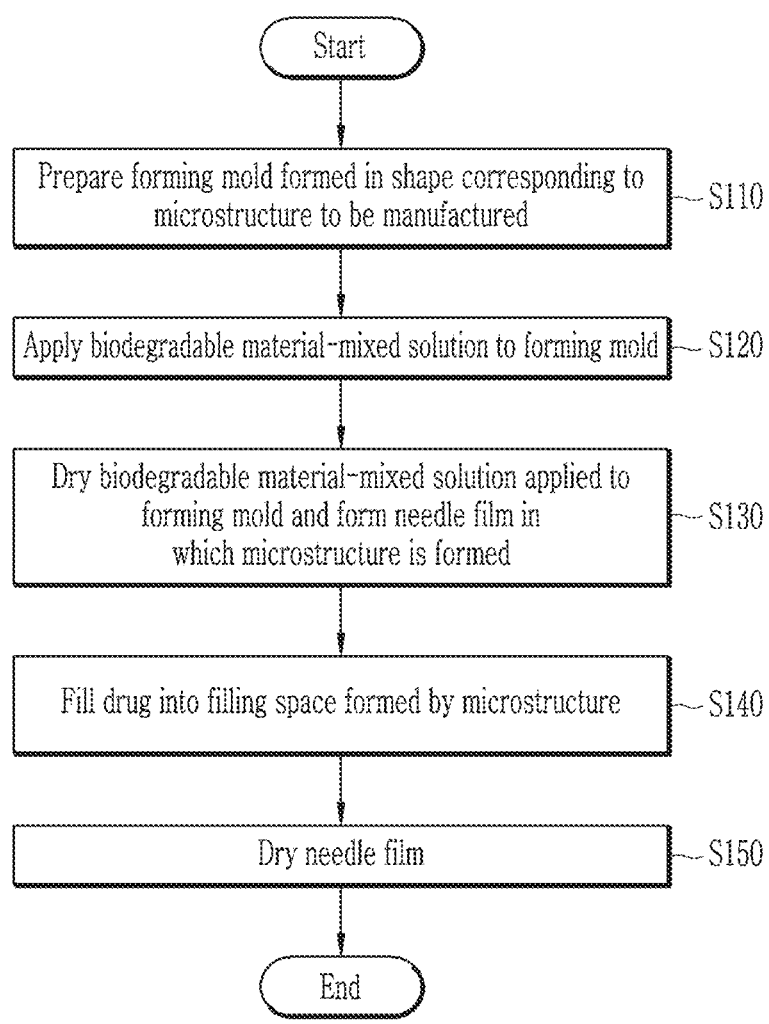
FIG. 1 is provided for description of a manufacturing method of a microstructure-based drug injection device according to a first embodiment of the present invention.

Hereinafter, the present invention will be described with reference to the accompanying drawing. However, the present invention may be implemented in various different forms, and therefore is not limited to the embodiments described herein. Accordingly, the drawings and description are to be regarded as illustrative in nature and not restrictive. Like reference numerals designate like elements throughout the specification.

In the entire specification, when a part is "connected (connected, contacted, combined)" with another part, it is not only "directly connected", but also "indirectly connected" with another member in the middle. In addition, when a part "includes" a certain constituent element, this means that other constituent elements may be further provided, rather than excluding other constituent elements, unless otherwise specified.

The terms used in the present specification are only used to describe a specific embodiment, and are not intended to limit the present invention. Expressions in the singular include expressions of plural, unless the context clearly indicates otherwise. In the present specification, terms such as "include" or "have" are intended to designate the existence of features, numbers, steps, actions, constituent elements, parts, or a combination of them described in the specification, and thus it is to be understood that the possibility of the presence or addition of one or more other features, elements, numbers, steps, actions, constituent elements, parts, or combinations thereof, is not preliminarily excluded.

Hereinafter, preferred embodiments of the present invention in which the above-described problem to be solved can be implemented in detail will be described with reference to the accompanying drawings. In describing the present embodiment, the same name and the same reference numeral are used for the same configuration, and additional descriptions thereof will be omitted below.

Referring to FIG. 1, a manufacturing method of a microstructure-based drug injection device according to a first embodiment of the present invention will now be described.

As shown in FIG. 1, a manufacturing method of a microstructure-based drug injection device according to a first embodiment includes preparing a forming mold (S110), applying a biodegradable material-mixed solution (S120), primary drying (S130), drug filling (S140), and secondary drying (S150).

In the preparing of the forming mold (S110), a forming mold having a shape that corresponds to a microstructure to be manufactured is prepared.

In the applying of the biodegradable material-mixed solution (S120), a biodegradable material-mixed solution is applied to an upper region of the forming mold.

In the primary drying (S130), the biodegradable material-mixed solution applied to the forming mold is dried to form a needle film where the micro structure is formed. In this case, the needle film having undergone the primary drying (S130) may be in a semi-dried state.

In the drug filling (S140), a drug is filled in a part of a filling space formed by the microstructure.

In the secondary drying (S150), the needle film is dried, and an inner space in regions excluding the region where the drug is filled is formed in the filling space, which has undergone the secondary drying (S150), and a gas is accommodated in the inner space.

Here, it is preferred that the drug filling (S140) and the secondary drying (S150) are repeated until an effective component contained in the drug is accommodated in the microstructure in the amount that must penetrate the human skin.

Since the inner space is formed in the microstructure of the microstructure-based drug injection device manufactured through the above-stated process, shrinkage of the microstructure during the primary drying (S130) and the secondary drying (S150) can be reduced, thereby producing a microstructure that is close to the shape of the forming mold.

Figure 8:
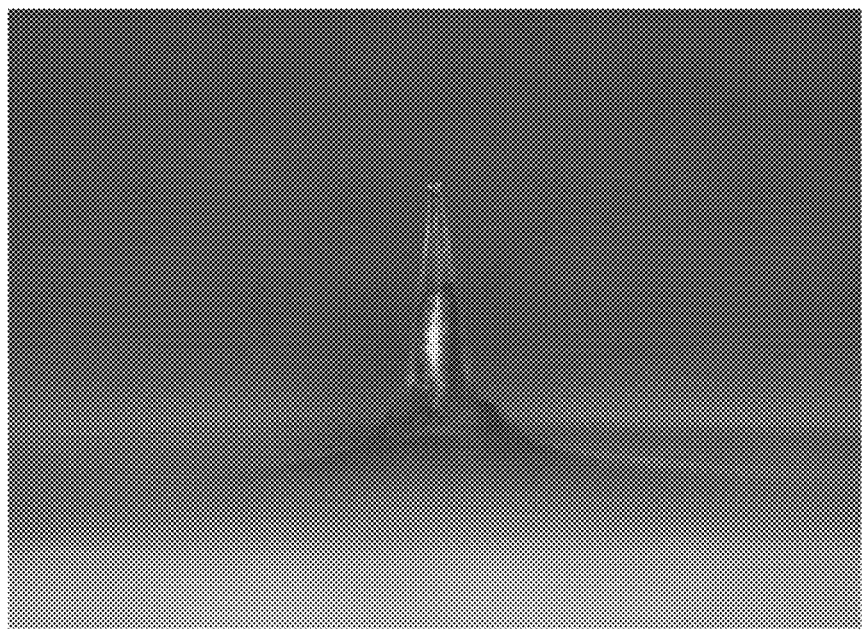
FIG. 8 is a photograph of a microstructure-based drug injection device manufactured by using the manufacturing method of the microstructure-based drug injection device according to the first embodiment of the present invention.

Thus, the microstructure-based drug injection device can be manufactured as shown in FIG. 8 using the manufacturing method of the microstructure-based drug injection device according to the first embodiment of the present invention.

Figure 2:
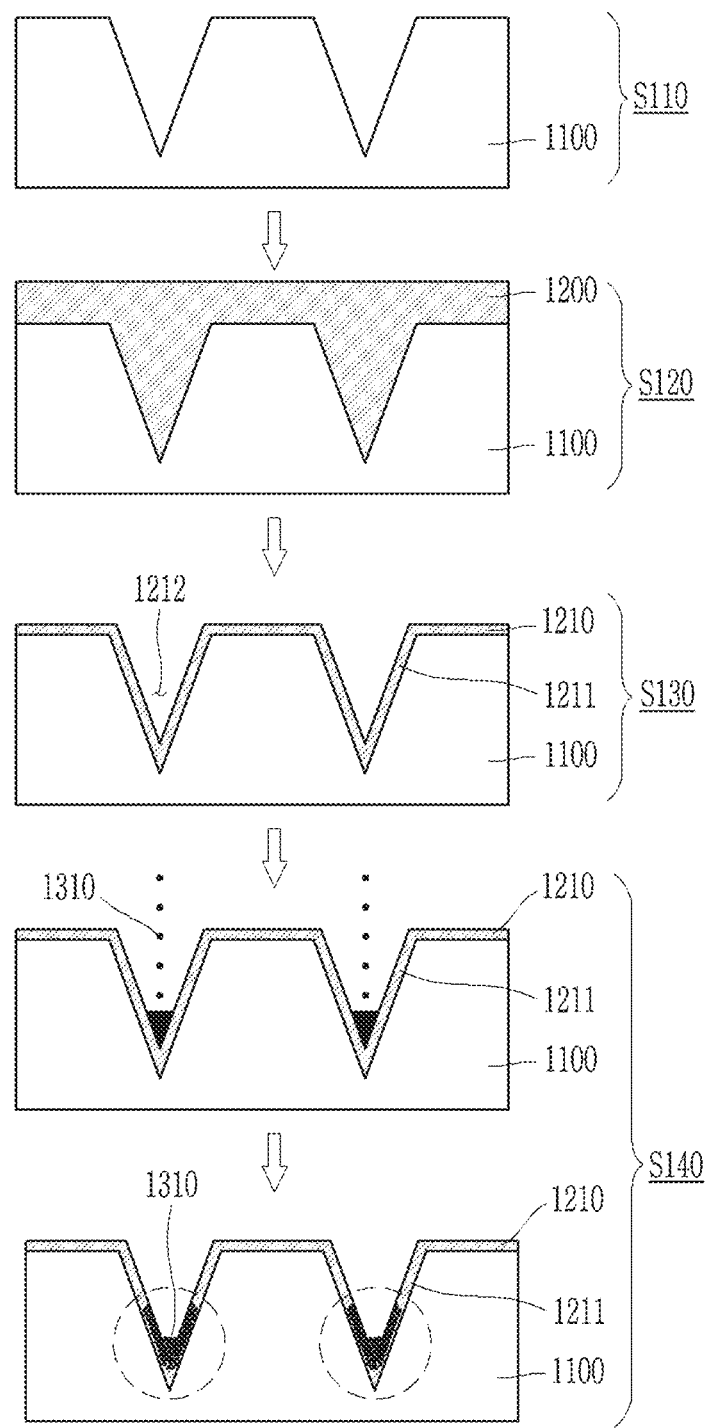
FIG. 2 is provided for description of a manufacturing method of a microstructure-based drug injection device according to a second embodiment of the present invention.

Referring to FIG. 2, a manufacturing method of the microstructure-based drug injection device according to a second embodiment will now be described.

As shown in FIG. 2, a manufacturing method of the microstructure-based drug injection device according to a second embodiment includes preparing a forming mold (S110), applying a biodegradable material-mixed solution (S120), primary drying (S130), and drug filling (S140), and although it is not illustrated in FIG. 2, secondary drying is also included.

A forming mold having a shape that corresponds to a micro structure to be manufactured is prepared in the preparing of the forming mold (S110), and a biodegradable material-mixed solution is wholly applied to an upper region of the forming mold in the applying of the biodegradable material-mixed solution (S120).

Accordingly, a needle film 1210 (S130) can be manufactured with a uniform thickness. That is, when the biodegradable material-mixed solution 1200 is applied to the upper portion of the forming mold 110 with a constant thickness, the biodegradable material-mixed solution 1200 is collected at the end of the shape of the forming mold 110, which corresponds to the microstructure 1211, due to a characteristic of the fluid such that the needle film 1210 with non-uniform thickness is formed, and thus in the applying of the biodegradable material-mixed solution (S120), as shown in FIG. 2, the biodegradable material-mixed solution 1200 is applied to the entire upper region of the forming mold 1100.

Although it is not specifically illustrated in FIG. 2, in the biodegradable material-mixed solution (S120), after the biodegradable material-mixed solution 1200 is wholly applied to the forming mold 1100, a process for etching is carried out after precipitation of the effective materials of the biodegradable material-mixed solution 1200 is carried out or the biodegradable material-mixed solution 1200 is preliminarily dried such that the biodegradable material-mixed solution 1200 has a constant thickness, and a needle film 1210 having a shape corresponding to the shape of the final finished microstructure-based drug injection device can be formed.

Here, a biodegradable material of the biodegradable material-mixed solution 1200 is a material that can be dissolved or decomposed in the body, and may be formed of a group consisting of polysaccharides such as nucleic acid, deoxyribonucleic acid, (DNA), ribonucleic acid (RNA), polydeoxyribonucleotide (PDRN), hyaluronic acid, alginic acid, pectin, carrageenan, chondroitin (sulfate), chondroitin sulfate, glycogen, dextran (sulfate), dextran, dextrin, keto acid, polylysine, collagen, gelatin, carboxymethyl chitin, fibrin, agarose, and pullulan, or proteins such as collagen, gelatin and hydrolysates thereof, or a group consisting of pullulan polyanhydride, polyester ester, polycaprolactone, polyesteramide, poly(butyric acid), poly(Valeric acid), polyurethane, polyacrylate, ethylene-vinyl acetate polymer, acryl substituted cellulose acetate, non-degradable polyurethane, polystyrene, polyvinyl chloride, polyvinyl fluoride, poly(vinyl imidazole), chlorosulfonate polyolefins, polyethylene oxide, polyvinylpyrrolidone (PVP), polyvinyl alcohol, polyethylene glycol (PEG), polymethacrylate, polyacrylic acid, carboxy vinyl polymer, hydroxypropyl methylcellulose, ethyl cellulose (EC), hydroxypropyl cellulose (HPC), carboxymethylcellulose, cyclodextrin, and copolymer and cellulose of monomers that form these polymers In addition, in the biodegradable material-mixed solution (S120), the amount of the biodegradable material-mixed solution 1200 applied to the forming mold 1100 can be adjusted according to a size and a thickness of the finally finished needle film 1210.

In the primary drying (S130), the biodegradable material-mixed solution 1200 applied to the forming mold 1100 is dried and thus the needle film 1210 where the microstructure 1211 is formed is produced.

That is, in the primary drying (S130), the forming mold 1100 to which the biodegradable material-mixed solution 1200 is applied is dried in a separate drying unit (not shown) for a predetermined time period at a predetermined temperature such that the needle film 1210 is formed. For example, a drying condition of the primary drying (S130) includes a temperature condition of 0° C. to 100° C., and the forming mold 1100 can be dried in a drying unit for several minutes to several hours.

In this case, the microstructure 1211 may have a length that can reach a desired position up to the subcutaneous tissue of the skin, and the length may be 10 μm to 10,000 μm. In addition, the filling space 1212 formed by the microstructure, that is, an area that is formed to be the inner space 1212a (refer to FIG. 10) later, reduces shrinkage of the microstructure 1211 in the primary drying (S130) such that the microstructure 1211 having a shape that is close to the shape of the forming mold 1100 can be manufactured.

In the drug filling (S140), a drug 1210 is filled in the filling space formed by the microstructure 1211.

Specifically, the drug 1310 is in a fluid state, and the drug 1310 is filled in the filling space 1212 formed by the microstructure 1211 in the drug filling (S140), and in this case, the amount of drug 1310 filled in the filling space 1212 is proportional to the amount of effective component that must penetrate the human skin.

A diameter k (refer to FIG. 10) of the drug 1310 filled in the filling space 1212 in the drug filling (S140) has a range within 1000 μm, and a minimum size of the diameter of the drug 1310 is the size of a droplet that can be manufactured, and it may be a nano-unit or a smaller unit within the manufacturing range.

The reason for limiting the diameter of the drug 1310 is to allow the drug 1310 in the form of droplets to move easily into a hole formed in the needle film 1210 and to precisely control the amount of drug filling. Here, the needle film 1210 is formed of a porous material, and the hole is formed in the needle film 1210 according to a characteristic of the needle film 1210 formed of the porous material.

Thus, in the drug filling (S140), at least some of the drug 1310 filled in the microstructure 1211 is permeated into the hole formed in the microstructure 1211, and the drug is filled in a part of the hole formed in the microstructure 1211 and a part of the filling space 1212, and this will be described in detail later.

After that, the needle film 1210 is dried in the secondary drying, and although it is not illustrated in the secondary drying in FIG. 2, the secondary drying according to a second embodiment will be described using the configuration and reference numerals shown in FIG. 2 to help understand the secondary drying according to the second embodiment.

Specifically, in the secondary drying, the needle film 1210 formed in the forming mold 1100 is dried in a separate drying unit for a predetermined time period at a predetermined temperature such that the drug 1310 may have mechanical strength that allows the microstructure 1211 in the area where the drug has penetrated to have sufficient mechanical strength to penetrate the skin, and in this case, an inner space 1212a (refer to FIG. 10) is formed in the filling space 1212.

For example, a temperature condition of the secondary drying is 0° C. to 80° C., and the needle film 1210 is dried for several minutes to several hours.

Here, the reason that a temperature condition maximum value in the secondary drying is lower than that of the primary drying (S130) is to prevent the drug droplets from being dried before contacting the needle film 1210 during the filling process, and the needle film 1210 from being distorted by heat.

In addition, the filling space 1212 formed by the microstructure 1211, that is, an area that is formed to be the inner space 1212a (refer to FIG. 10), later reduces shrinkage of the microstructure 1211 in the secondary drying such that the microstructure 1211 having a shape that is close to the shape of the forming mold 1100 can be manufactured.

Resultantly, the microstructure 1211 is dried and has sufficient mechanical strength to penetrate human skin by performing the secondary drying.

The needle film 1210 where the microstructure 1211 is formed through the above-described process, and in an upper area of the needle film 1210, that is, an area opposite to a direction in which the microstructure 1211 protrudes, a patch film (not shown) for attaching the needle film 1210 to the human skin is adhered.

When the needle film 1210 to which the patch film is adhered is attached to the skin and the microstructure 1211 is inserted into the subcutaneous tissue and dissolved, the area where the inner space 1212a (refer to FIG. 10) of the microstructure 1211, that is, of which one side of the microstructure 1211 contacts the subcutaneous tissue and the other side contacts the inner space, is quickly dissolved such that the patch film and the attached needle film can be quickly separated from the skin while the microstructure 1211 in the area filled with the drug 1310 is being inserted into the subcutaneous tissue.

In addition, when an external force is applied to attach the needle film to the skin and insert the microstructure into the skin, the inner space is formed in the microstructure 1211 such that the drug 1310 accommodated in the microstructure 1211 can be prevented from being leaked out between the needle film 1210 and the patch film due to the external force.

Figure 3:
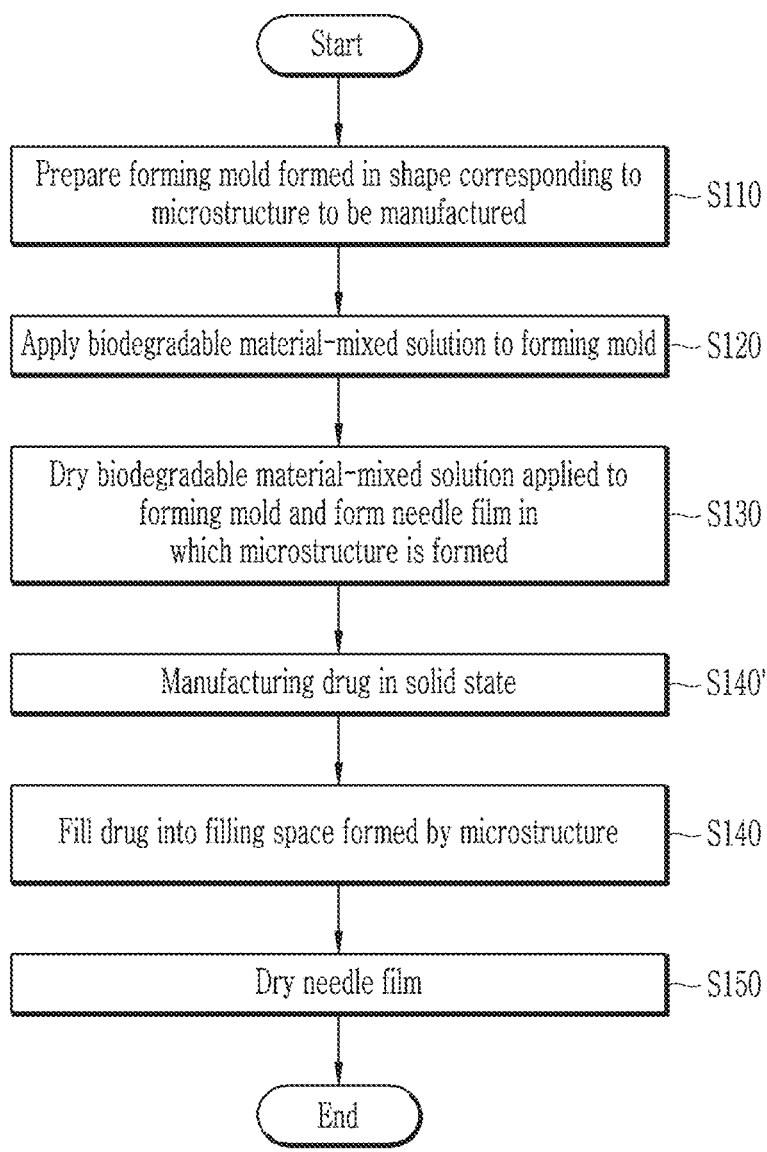
FIG. 3 is provided for description of a manufacturing method of a microstructure-based drug injection device according to a third embodiment of the present invention.
Figure 4:
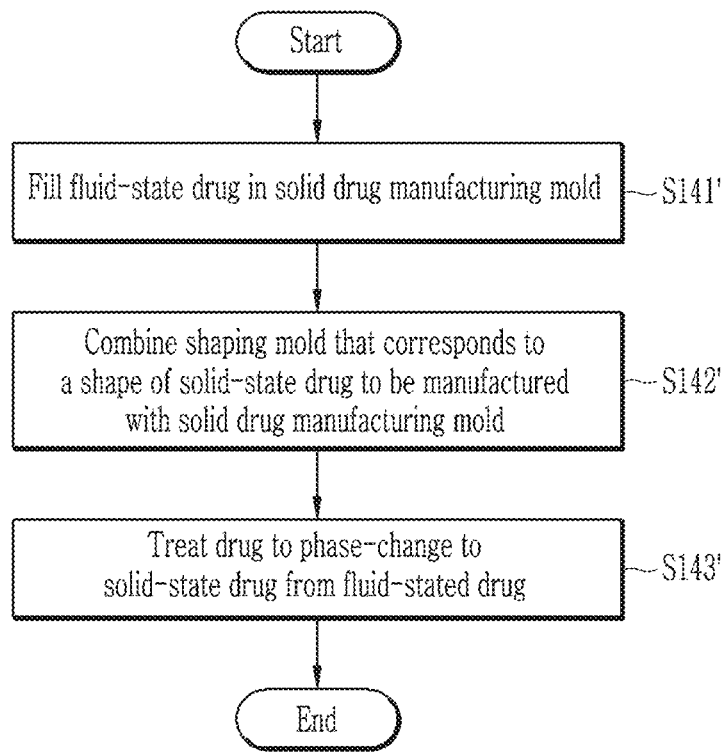
FIG. 4 is provided for description of manufacturing a solid-state drug in the manufacturing method of a microstructure-based drug injection device of FIG. 3.

Referring to FIG. 3 and FIG. 4, a manufacturing method of a microstructure-based drug injection device according to a third embodiment according to the present invention will be described.

As shown in FIG. 3, a manufacturing method of a microstructure-based drug injection device according to a third embodiment includes preparing a forming mold (S110), applying a biodegradable material-mixed solution (S120), primary drying (S130), manufacturing a solid drug (S140'), drug filling (S140), and secondary drying (S150).

The preparing of the forming mold (S110), the applying of the biodegradable material-mixed solution (S120), the primary drying (S130), and the secondary drying (S150) included in the manufacturing method of the microstructure-based drug injection device according to the third embodiment correspond to the preparing of the forming mold (S110), the applying of the biodegradable material-mixed solution (S120), the primary drying (S130), and the secondary drying (S150) included in the manufacturing method of the microstructure-based drug injection device according to the first and second embodiments, and detailed descriptions will be omitted.

In addition, the drug filling (S140) of the third embodiment is different from the drug filling (S140) of the first and second embodiments due to the solid drug manufacturing (S140'), and this will be described later.

The solid drug manufacturing (S140') is carried out after the primary drying (S130), and a drug in a solid state, filled in the filling space in the drug filling (S140), is manufactured.

Specifically, as shown in FIG. 4, the solid drug manufacturing (S140') includes fluid drug filling (S142'), mold combining (S142'), and drug treatment (S143').

In the fluid drug filling (S141'), a drug in a fluid state is filled in a solid drug forming mold.

In the mold combining (S142'), a shape mold that corresponds to a shape of a solid-state drug to be manufactured is combined with the solid drug forming mold. In this case, the shape mold in the mold combining is formed with a structure in which the drug is provided in only a part of the filling space.

In the drug treatment (S143'), the drug is treated so that the fluid drug phase changes to the solid drug phase, and for example, treatment of the drug can change the phase of the drug by performing processes such as heating, drying, or irradiation with ultraviolet rays, depending on the type of the drug.

After the above-described solid drug manufacturing (S140'), the solid-state drug is filled by being inserted into the filling space formed by the microstructure, and in this case, an inner space is formed in an area other than the area in which the drug is accommodated in the filling space, and a gas is accommodated in the inner space.

Since the inner space is formed in the microstructure of the microstructure-based drug injection device manufactured through the above-stated process, shrinkage of the microstructure during the primary drying (S130) and the secondary drying (S150) can be reduced, thereby producing a microstructure that is close to the shape of the forming mold.

Figure 5:
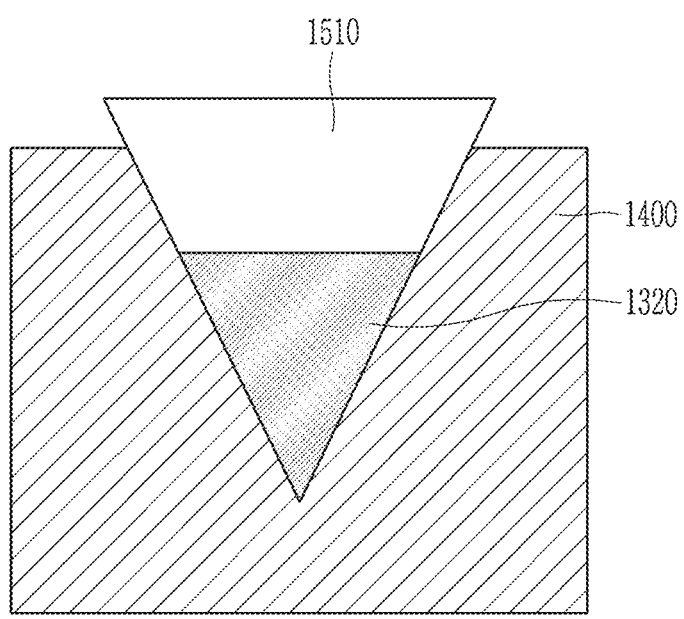
FIG. 5 is provided for description of a manufacturing method of a microstructure-based drug injection device according to a fourth embodiment of the present invention.

Referring to FIG. 5 a manufacturing method of the microstructure-based drug injection device according to a fourth embodiment of the present invention will be described.

A manufacturing method of the microstructure-based drug injection device according to a fourth embodiment includes preparing a forming mold, applying a biodegradable material-mixed solution, primary drying, manufacturing a solid drug, drug filling, and secondary drying.

Here, the preparing of the forming mold, the applying of the biodegradable material-mixed solution, the primary drying, the drug filling, and the secondary drying according to the fourth embodiment correspond to the preparing of the forming mold (S110), the applying of the biodegradable material-mixed solution (S120), the primary drying (S130), the drug filling (S140), and the secondary drying (S150) according to the third embodiment, and therefore no further description will be provided.

However, the manufacturing of the solid drug of the manufacturing method of the microstructure-based drug injection device according to the fourth embodiment includes fluid drug filling, mold combining, and drug treatment like the solid drug manufacturing (S140') of the third embodiment, but the solid-state drug manufactured in the manufacturing of the solid drug is formed in the shape of a triangle.

Specifically, as shown in FIG. 5, in the manufacturing of the solid drug of the manufacturing method of the microstructure-based drug injection device according to the fourth embodiment, a process for filling a drug 1320 in a fluid state to a solid drug manufacturing mold 1400 is carried out in the fluid drug filling, and after that, a shaping mold 1510 is combined with the solid drug manufacturing mold 1400 and changes a shape of the drug 1320 in the mold combining such that a drug in a liquid state is phase-changed to a drug in a solid state.

That is, in the present embodiment, a shape of the shaping mold 1510 forms a shape of the drug 1320 to be a triangle that corresponds to an internal shape of the filling space, and the shaping mold 1510 is disposed in at least a part of the filling space, thereby combining the solid drug manufacturing mold 1400 such that the shape of the drug 1320 can be manufactured.

Thus, a microstructure-based drug injection device (refer to FIG. 11) in which the drug 1320 is manufactured in a solid triangle shape, and accordingly, the drug 1320 is inserted and filled in a part of the filling space in the drug filling, and an inner space is formed in the filling space can be formed.

The shape of the drug 1320 manufactured according to the fourth embodiment may have a shape that is evenly filled in a front end of the filling space as shown in FIG. 5, but the drug may be filled so that it is skewed to one side, and the triangle shape of the drug 1320 can be freely formed.

Figure 6:
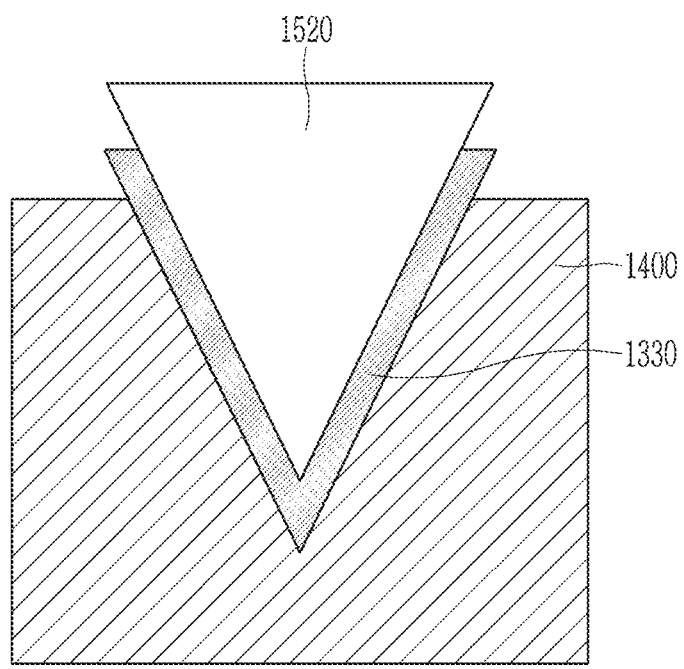
FIG. 6 is provided for description of a manufacturing method of a microstructure-based drug injection device according to a fifth embodiment of the present invention.

Referring to FIG. 6, a manufacturing method of a microstructure-based drug injection device according to a fifth embodiment of the present invention will be described.

A manufacturing method of a microstructure-based drug injection device according to a fifth embodiment includes preparing a forming mold, applying a biodegradable material-mixed solution, primary drying, manufacturing a solid drug, drug filling, and secondary drying.

Here, the preparing of the forming mold, the applying of the biodegradable material-mixed solution, the primary drying, the drug filling, and the secondary drying according to the fifth embodiment correspond to the preparing of the forming mold (S110), the applying of the biodegradable material-mixed solution (S120), the primary drying (S130), the drug filling (S140), and the secondary drying (S150) according to the third embodiment, and therefore no further description will be provided.

However, the manufacturing of the solid drug of the manufacturing method of the microstructure-based drug injection device according to the fifth embodiment includes fluid drug filling, mold combining, and drug treatment like the solid drug manufacturing (S140') of the third embodiment, but the solid-state drug manufactured in the manufacturing of the solid drug is formed in the shape of a "V", and part of it is disposed in a part of the filling space, while the other part is formed in a shape that is disposed outside of the filling space.

Specifically, in the manufacturing of the solid drug of the manufacturing method of the microstructure-based drug injection device according to the fifth embodiment, a process for filling a drug 1330 in a fluid state in a solid drug manufacturing mold 1400 is carried out in the solid drug filling as shown in FIG. 6, and after that, a shaping mold 1520 is combined with the solid drug manufacturing mold 1400 and changes a shape of the drug 1330 in the mold combining such that a drug in a liquid state is phase-changed to a drug in a solid state.

That is, in the present embodiment, the shaping mold 1520 is formed in the shape of a "V" such that the drug 1330 is formed in the shape of a "V", but some of the drug 1330 is disposed in at least a part of a filling space and the other is disposed outside the filling space, and the shaping mold 1520 is combined with the solid drug manufacturing mold 1400 such that the shape of the drug 1330 can be manufactured.

Accordingly, a microstructure-based drug injection device (refer to FIG. 12) in which the drug 1330 is in a solid state and is formed in the shape of a "V", but some of the drug 1330 is disposed in at least a part of the filling space and the other part is disposed outside the filling space in the during filling, and accordingly, the drug 1330 is inserted and filled in at least a part of the filling space in the drug filling, and an inner space in the filling space can be formed.

The shape of the drug 1330 manufactured according to the fifth embodiment is not restrictive, and opposite ends of the drug 1330, which correspond to the other portion of the drug 1330 may have the length as shown in FIG. 6, or may have different lengths. In this case, one end may be disposed inside the filling space, and the other end may be disposed outside the filling space.

Figure 7:
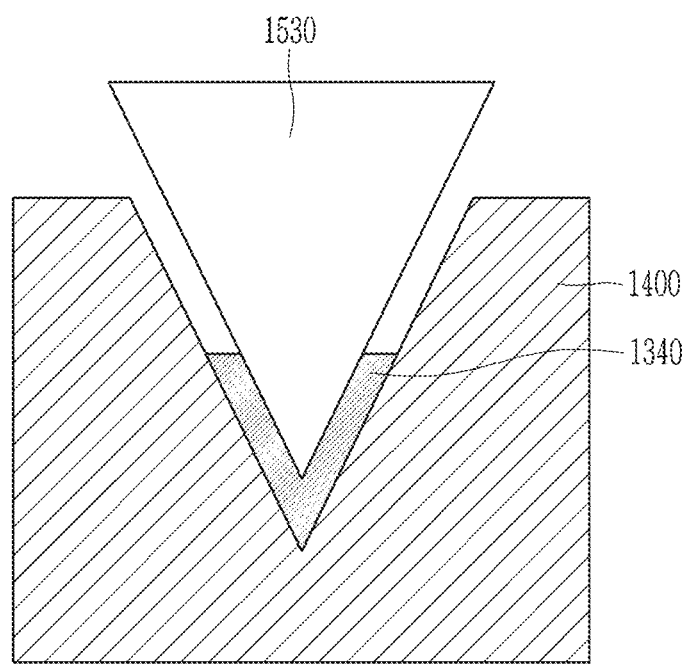
FIG. 7 is provided for description of a manufacturing method of a microstructure-based drug injection device according to a sixth embodiment of the present invention.

Referring to FIG. 7, a manufacturing method of the microstructure-based drug injection device according to a sixth embodiment of the present invention will be described.

A manufacturing method of a microstructure-based drug injection device according to a sixth embodiment includes preparing a forming mold, applying a biodegradable material-mixed solution, primary drying, manufacturing a solid drug, drug filling, and secondary drying.

Here, the preparing of the forming mold, the applying of the biodegradable material-mixed solution, the primary drying, the drug filling, and the secondary drying according to the sixth embodiment correspond to the preparing of the forming mold (S110), the applying of the biodegradable material-mixed solution (S120), the primary drying (S130), the drug filling (S140), and the secondary drying (S150) according to the third embodiment, and therefore no further description will be provided.

However, the manufacturing of the solid drug of the manufacturing method of the microstructure-based drug injection device according to the fifth embodiment includes fluid drug filling, mold combining, and drug treatment like the solid drug manufacturing (S140') of the third embodiment, but the solid-state drug manufactured in the manufacturing of the solid drug is formed in the shape of a "V" and is disposed in a part of the filling space.

Specifically, in the manufacturing of the solid drug of the manufacturing method of the microstructure-based drug injection device according to the sixth embodiment, a process for filling a drug 1340 in a fluid state in a solid drug manufacturing mold 1400 is carried out in the solid drug filling as shown in FIG. 6, and after that, a shaping mold 1530 is combined with the solid drug manufacturing mold 1400 and changes a shape of the drug 1330 in the mold combining such that a drug in a liquid state is phase-changed to a drug in a solid state.

That is, in the present embodiment, the shaping mold 1530 is formed in the shape of a "V" and the drug 1330 is disposed in at least a part of a filling space, and the shaping mold 1520 is combined with the solid drug manufacturing mold 1400 such that the shape of the drug 1340 can be manufactured.

Accordingly, a microstructure-based drug injection device (refer to FIG. 11) in which the drug 1340 is in a solid state and is formed in the shape of a "V", while filling a part of the filling space, and accordingly, the drug 1340 is inserted and filled in a part of the filling space in the drug filling, and an inner space is formed in the filling space.

The shape of the drug 1340 manufactured according to the fifth embodiment is not restrictive, and opposite ends of the drug 1340, which correspond to the other portion of the drug 1340, may have the length as shown in FIG. 7, or may have different lengths.

Figure 9:
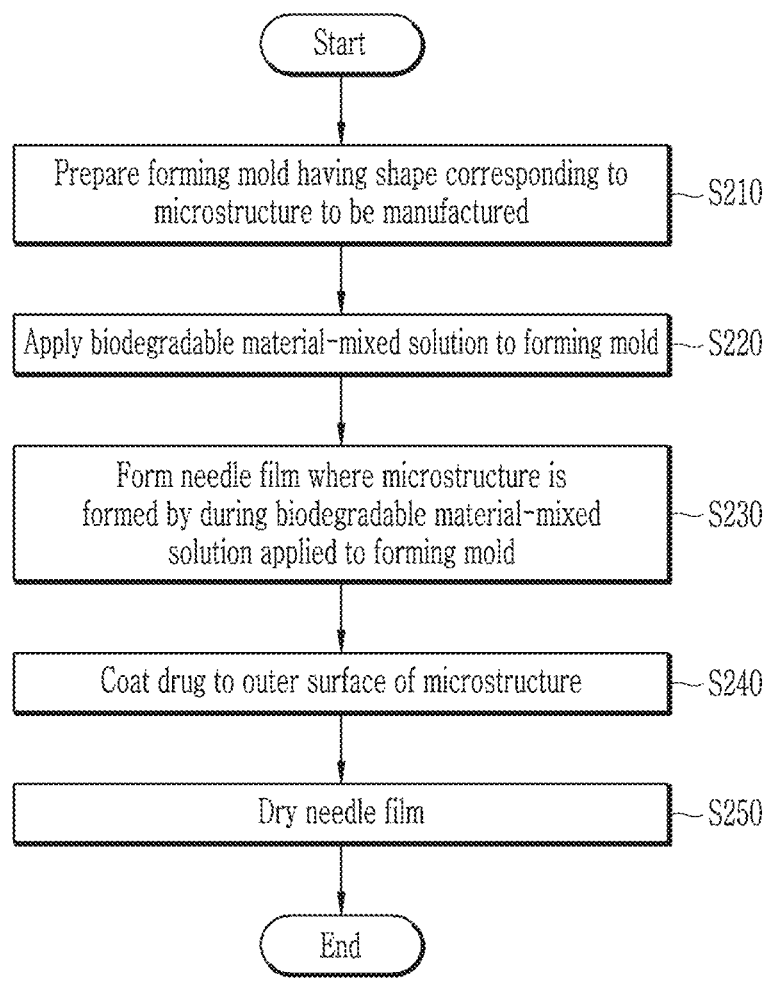
FIG. 9 is provided for description of a manufacturing method of a microstructure-based drug injection device according to a seventh embodiment of the present invention.

Referring to FIG. 9, a manufacturing method of the microstructure-based drug injection device according to a seventh embodiment of the present invention will be described.

As shown in FIG. 9, a manufacturing method of a microstructure-based drug injection device according to a seventh embodiment includes preparing a forming mold (S210), applying a biodegradable material-mixed solution (S220), primary drying (S230), drug coating (S240), and secondary drying (S250).

The preparing of the forming mold (S210), the applying of the biodegradable material-mixed solution (S220), the primary drying (S230), and the secondary drying (S250) according to the present embodiment correspond to the preparing of the forming mold (S110), the applying of the biodegradable material-mixed solution (S120), the primary drying (S130), and the secondary drying (S150) included in the manufacturing method of the microstructure-based drug injection device according to the first and second embodiments, and detailed descriptions will be omitted.

However, in the drug coating (S240) according to the present embodiment, the drug is coated on the outside of the microstructure.

For example, the drug is formed in a fluid state and applied to an outer surface of the microstructure in the drug coating (S240) such that the drug can be coated to the outer surface of the microstructure.

Alternatively, in the drug coating (S240), the drug is formed in a solid state and fitted to an outer surface of the microstructure such that the drug may be coated to the outer surface of the microstructure. In this case, the drug may be prepared through manufacturing a solid drug to be fitted into the outer surface of the microstructure before the drug coating (S240).

In this case, an inner space in which a gas is accommodated is formed in the filling space formed by the microstructure.

In a microstructure-based drug injection device according to the seventh embodiment, manufactured through the above-described process, a drug is coated to an outer side of the microstructure, and the inner space where a gas is accommodated is formed in the filling space formed by the microstructure such that it is possible to improve the skin penetration and efficiency delivery the effective component contained in the drug.

In addition, since the inner space is formed in the microstructure, shrinkage of the microstructure in the primary drying S230 and the secondary drying S250 can be reduced such that a microstructure of which a structure is close to a shape of a forming mold can be manufactured.

Next, referring to FIG. 10, a first manufacturing example of a microstructure-based drug injection device manufactured according to the above-described manufacturing method of the microstructure-based drug injection device according to the second embodiment will be described.

Figure 10:
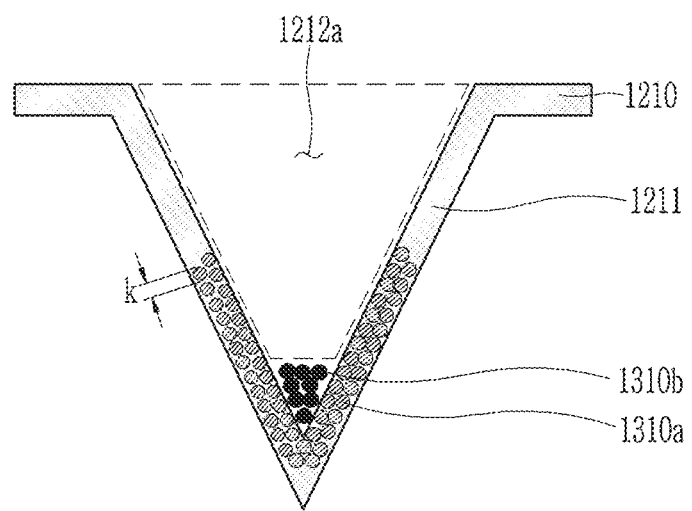
FIG. 10 shows a first manufacturing example of a microstructure-based drug injection device manufactured according to the manufacturing method of the microstructure-based drug injection device according to the second embodiment.

As shown in FIG. 10, a microstructure-based drug injection device according to a first manufacturing example includes a needle film 1210, drugs 1310a and 1310b, and an inner space 1212a.

The needle film 1210 is formed of a biodegradable material, and a microstructure 1211 is formed.

The drugs 1310a and 1310b are in a fluid state, and are filled in at least a part of a filling space 1212 (refer to FIG. 2) formed by the microstructure 1211, and a filling amount of the drugs 1310a and 1310b is proportional to an effective component that must be permeated into the human skin, while a droplet diameter k of the drugs 1310a and 1310b has a range within 1000 µm, and detailed description thereof is omitted since it has been described above.

In addition, the drugs 1310a and 1310b may contain any beneficial effective material that acts on or penetrates the skin. The effective material may be cosmetic ingredients such as vaccines, genes, antibodies, peptides, anesthetics, insulin, polysaccharides, proteins, synthetic organic compounds, synthetic inorganic compounds, or cosmetic components such as whitening compounds or antioxidants, or may be any other effective material permitted for pharmaceutical, medical, or cosmetic use.

In addition, the drug 1310 may contain a stabilizer. The stabilizing agent serves to stably maintain the effective material contained in the drug. As non-limiting examples, the stabilizer may be an ingredient such as albumin, nucleic acid, deoxyribonucleic acid (DNA), ribonucleic acid (RNA), or polydeoxyribonucleotide (PDRN), and may be any other stabilizer permitted for medical or cosmetic use.

In addition, as described in the manufacturing method of the microstructure-based drug injection device according to the second embodiment, at least some of the drug 1310a filled in the microstructure 1211 penetrates a hole formed in the microstructure 1211.

In this case, the needle film 1210 on which the microstructure 1211 is formed must be porous, a diameter of the hole formed in the needle film 1210 should be larger than the diameter of the drug 1310a, and accordingly, the drug 1310a can penetrate the needle film 1210, that is, the front end of the microstructure 1211.

In addition, an area occupied by the drug 1310b that is not penetrated into the microstructure 1211 and an inner space 1212a, which is the region of the filling space, are formed in the filling space, and the inner space 1212a is filled with a gas.

Accordingly, in the microstructure-based drug injection device according to the first embodiment, the filling space 1212 formed by the microstructure 1211 is filled with drugs, and some of the drugs 1310a penetrate the hole formed inside the microstructure 1211, thereby improving the skin penetration and delivery efficiency of the effective component contained in drugs 1310a and 1310b.

Next, referring to FIG. 11, a second manufacturing example of a microstructure-based drug injection device manufactured according to the above-described manufacturing method of the microstructure-based drug injection device according to the fourth embodiment will be described.

Figure 11:
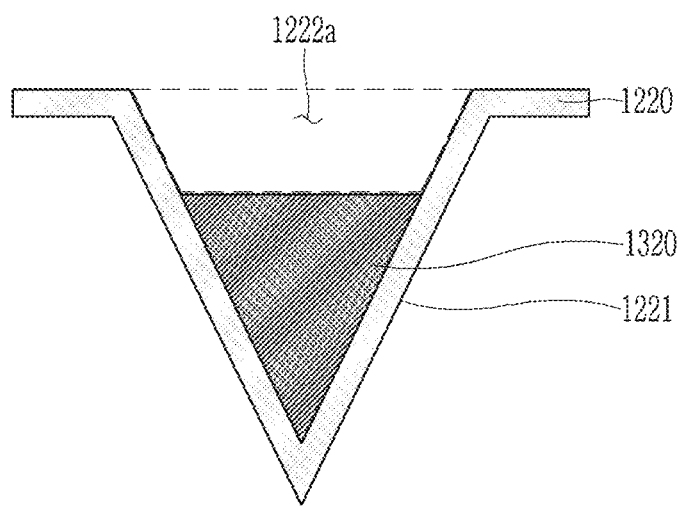
FIG. 11 shows a second manufacturing example of a microstructure-based drug injection device manufactured according to the manufacturing method of the microstructure-based drug injection device according to the fourth embodiment.

As shown in FIG. 11, a microstructure-based drug injection device according to a second manufacturing example includes a needle film 1220, a drug 1320, and inner space 1222a.

In this case, the drug 1320 of the microstructure-based drug injection device according to the second manufacturing example is in a solid state, and is formed in the shape of a triangle by the mold combining that is described with reference to FIG. 5 and is thus inserted and filled in a filling space (no referential numeral provide) formed by the microstructure 1221.

That is, the shape of the drug 1320 is a triangle that corresponds to an internal shape of the filling space, and thus the drug 1320 is disposed in at least a part of the filling space, and the inner space 1222a may be formed in an area other than the area where the drug 1320 is accommodated.

The needle film 1220 according to the second manufacturing example is the same as the needle film 1210 according to the above-described first manufacturing example, and thus no further description will be provided.

Next, referring to FIG. 12, a third manufacturing example of a microstructure-based drug injection device manufactured according to the above-described manufacturing method of the microstructure-based drug injection device according to the fifth embodiment will be described.

Figure 12:
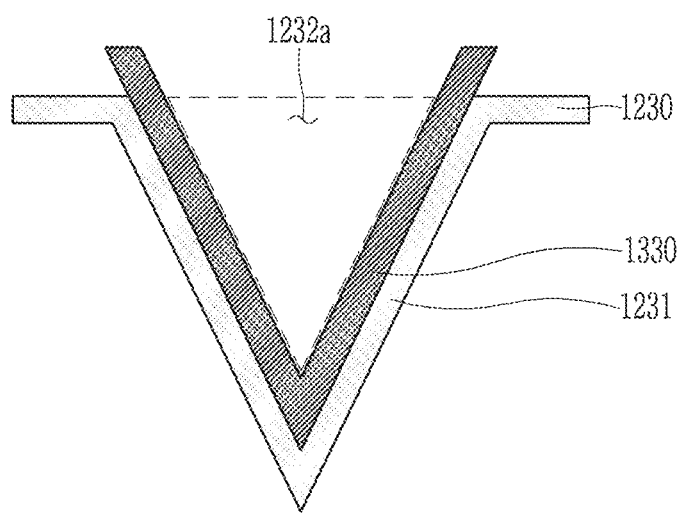
FIG. 12 shows a third manufacturing example of a microstructure-based drug injection device manufactured according to the manufacturing method of the microstructure-based drug injection device according to the fifth embodiment.

As shown in FIG. 12, a microstructure-based drug injection device according to a third manufacturing example includes a needle film 1230, a drug 1330, and an inner space 1232a.

In this case, the drug 1330 of the microstructure-based drug injection device according to the third manufacturing example is in a solid state, and is formed in the shape of a "V" by the molding combining described with reference to FIG. 6 and is thus inserted and filled in a filling space (no referential numeral provided) formed by the microstructure 1231.

That is, the shape of the drug 1330 is a "V", and a part of the drug 1330 is disposed in at least a part of the filling space and the other part is disposed outside the filling space, and thus the inner space 1232a may be formed in an area other than the area where the drug 1330 is accommodated.

The needle film 1230 according to the second manufacturing example is the same as the needle film 1210 according to the above-described first manufacturing example, and thus no further description will be provided.

Next, referring to FIG. 13, a fourth manufacturing example of a microstructure-based drug injection device manufactured according to the above-described manufacturing method of the microstructure-based drug injection device according to a sixth embodiment will be described.

Figure 13:
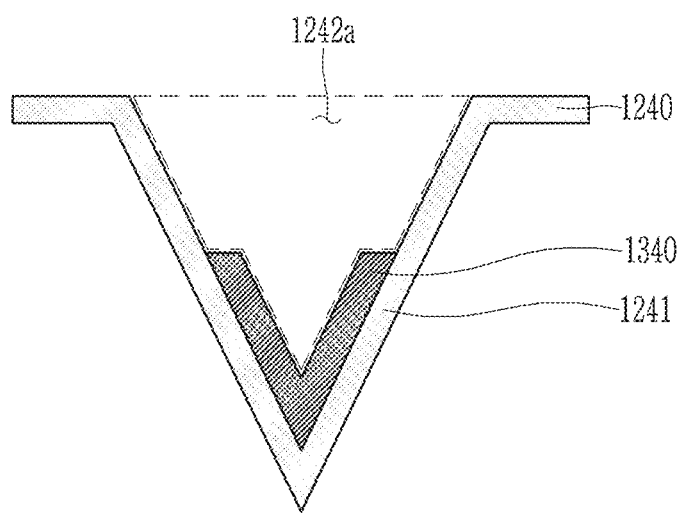
FIG. 13 shows a fourth manufacturing example of a microstructure-based drug injection device manufactured according to the manufacturing method of the microstructure-based drug injection device according to the sixth embodiment.

As shown in FIG. 13, a microstructure-based drug injection device according to a fourth manufacturing example includes a needle film 1240, a drug 1340, and an inner space 1242a.

In this case, the drug 1340 of the microstructure-based drug injection device according to the fourth manufacturing example is in a solid state, and is formed in the shape of a "V" by the molding combining described with reference to FIG. 7, and is thus inserted and filled in a filling space (no referential numeral provided) formed by the microstructure 1241.

That is, the shape of the drug 1330 is the "V" and a part of the drug 1340 is disposed in at least a part of the filling space, and thus the inner space 1242a is formed in area other than the area where the drug 1330 is accommodated.

The needle film 1230 according to the fourth manufacturing example is the same as the needle film 1210 according to the above-described first manufacturing example, and thus no further description will be provided.

Figure 14:
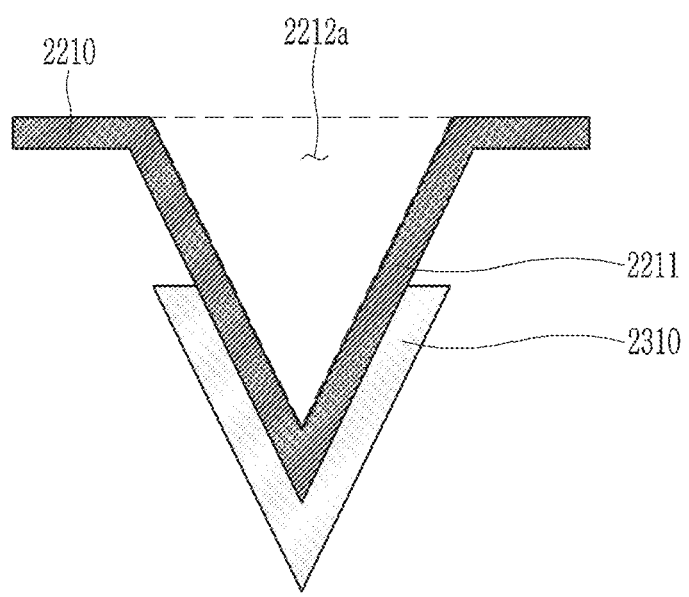
FIG. 14 shows a fifth manufacturing example of a microstructure-based drug injection device manufactured according to the manufacturing method of the microstructure-based drug injection device according to the seventh embodiment.

Next, referring to FIG. 14, a fifth manufacturing example of a microstructure-based drug injection device manufactured according to the above-described manufacturing method of the microstructure-based drug injection device according to a seventh embodiment will be described.

A microstructure-based drug injection device according to another embodiment includes a needle film 2210, a drug 2310, and a microstructure 2211.

The needle film 2210 of the microstructure-based drug injection device according to the present embodiment is the same as the needle film of the above-described first manufacturing example of the microstructure-based drug injection device, and therefore no further description will be provided.

However, the drug 2310 of the microstructure-based drug injection device according to the present embodiment is coated on an outer surface of the microstructure 2211. That is, the drug 2310 may be formed in a fluid state and applied to an outer surface of the microstructure 2211 such that the drug 2310 can be coated to the outer surface of the microstructure 2211, or the drug 2310 may be formed in a solid state and fitted to an outer surface of the microstructure 2211 such that the drug 2310 may be coated to the outer surface of the microstructure 2211.

The inner space 2212a is disposed in the filling space formed by the microstructure 2211, and a gas is accommodated therein.

In addition, since the detailed description of the microstructure-based drug injection device according to the present invention is the same as the manufacturing method of the microstructure-based drug injection device described above, a description thereof will be omitted.

While this invention has been described in connection with what is presently considered to be practical embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS

1100: forming mold
1200: biodegradable material-mixed solution
1210, 1220, 1230, 1240, 2210: needle film
1211, 1221, 1231, 1241, 2211: microstructure
1212: filling space
1212a, 1222a, 1232a, 1242a, 2212a: inner space
1310, 1320, 1330, 1340, 2310: drug
1400: solid drug manufacturing mold
1510, 1520, 1530: shaping mold

The invention claimed is:

1. A method for manufacturing a microstructure-based drug injection device, comprising:
preparing a forming mold having a shape that corresponds to a microstructure to be manufactured;
applying a biodegradable material-mixed solution to the forming mold;
primary drying at a first temperature to form a needle film where the microstructure is formed by drying the biodegradable material-mixed solution applied to the forming mold;
drug filling for filling a drug in a filling space formed by the microstructure; and
secondary drying at a second temperature less than the first temperature to dry the needle film subsequent to the drug filling,
wherein an inner space is formed in an area other than an area where the drug is accommodated in the filling space that has undergone the secondary drying.

2. The method for manufacturing the microstructure-based drug injection device of claim 1, wherein:
the drug filled in the filling space is in a fluid state in drug filling; and
at least a part of the drug filled in the filling space is permeated into the microstructure in the drug filling.

3. The method for manufacturing the microstructure-based drug injection device of claim 2, wherein
a droplet diameter of the drug filled in the filling space in the drug filling has a range within 1000 μm.

4. The method for manufacturing the microstructure-based drug injection device of claim 1, further comprising, before the drug filling, manufacturing a solid-state drug filled in the filling space,
wherein the manufacturing of the solid-state drug comprises:
fluid-state drug filling for filling a fluid-state drug in a solid drug manufacturing mold;
mold combining in which a shaping mold that corresponds to a shape of the solid-state drug to be manufactured is combined with the solid drug manufacturing mold; and
drug treatment in which the drug is treated to be phase-changed to the solid-state drug from the liquid-state drug.

5. The method for manufacturing the microstructure-based drug injection device of claim 4, wherein
in the mold combining, the shaping mold forms the drug in the shape of a triangle in a cross-section view corresponding to an inner shape of the filling space in the cross-section view while disposing the drug in a part of the filling space, and is combined with the solid drug manufacturing mold.

6. The method for manufacturing the microstructure-based drug injection device of claim 4, wherein
in the mold combining, the shaping mold forms the drug in the shape of a "V", in a cross-section view, while disposing a first part of the drug in a part of the filling space and disposing a second part of the drug outside the filling space, and
the drug in the shape of the "V" is combined with the solid drug manufacturing mold.

7. The method for manufacturing the microstructure-based drug injection device of claim 4, wherein
in the mold combining, the shaping mold forms the drug in the shape of a "V", in a cross-section view, while disposing the drug in a part of the filling space, and
the drug in the shape of the "V" is combined with the solid drug manufacturing mold.

8. A method for manufacturing a microstructure-based drug injection device, comprising:
preparing a forming mold having a shape that corresponds to a microstructure to be manufactured;
applying a biodegradable material-mixed solution to the forming mold;
primary drying at a first temperature to form a needle film where the microstructure is formed by drying the biodegradable material-mixed solution applied to the forming mold;
coating a drug to an outer surface of the microstructure; and
secondary drying at a second temperature less than the first temperature to dry the needle film subsequent to the drug filling,
wherein an inner space where a gas is accommodated is formed in a filling space formed by the microstructure in the primary drying.

9. A microstructure-based drug injection device, comprising:

a needle film having a microstructure, wherein the microstructure has a V-shape in a cross-section view, and the microstructure has an inner surface facing an interior of the V-shape in the cross-section view and an outer surface facing away from the V-shape in the cross-section view, with a filling space of the microstructure being defined by the inner surface; and a drug filled in a part of the filling space of the microstructure and filled in a part of the microstructure between the inner surface and the outer surface, wherein a portion of the filling space free from being filled with the drug is filled with a gas.

10. The microstructure-based drug injection device of claim 9, wherein the drug is in a fluid state, and at least a part of the drug filled in the filling space is permeated into the microstructure.

11. The microstructure-based drug injection device of claim 10, wherein a droplet diameter of the drug has a range within 1000 μm.

12. The microstructure-based drug injection device of claim 9, wherein the drug is in a solid state, and the drug filled in the part of the filling space is formed in the shape of a triangle in the cross-section view corresponding to an inner shape of the filling space in the cross-section view.

13. The microstructure-based drug injection device of claim 9, wherein the drug is in a solid state, and the drug is formed in the shape of a "V", in the cross-section view, with a first part of the drug filled in the part of the filling space and a second part being outside the filling space.

14. The microstructure-based drug injection device of claim 9, wherein the drug is in a solid state, and the drug filled in the part of the filling space is formed in the shape of a "V", in the cross-section view.

15. A microstructure-based drug injection device-device, comprising:

a needle film having a microstructure, wherein the microstructure has a V-shape in a cross-section view, and the microstructure has an inner surface facing an interior of the V-shape in the cross-section view and an outer surface facing away from the V-shape in the cross-section view, with a filling space of the microstructure being defined by the inner surface;

a drug coated to an outer surface of the microstructure; and the filling space is at least partially filled with a gas.

* * * * *